United States Patent
Smarrito-Menozzi et al.

(10) Patent No.: US 10,787,481 B2
(45) Date of Patent: *Sep. 29, 2020

(54) SUGAR-DIPEPTIDE CONJUGATES AS FLAVOR MOLECULES

(71) Applicant: NESTEC S.A., Vevey (CH)

(72) Inventors: Candice Marie Smarrito-Menozzi, Belmont-sur-Lausanne (CH); Florian Viton, Lausanne (CH); Thomas Hofmann, Neufahrn (DE); Maximilian Kranz, Freising (DE)

(73) Assignee: Societe des Produits Nestle S.A., Vevey (CH)

( * ) Notice: Subject to any disclaimer, the term of this patent is extended or adjusted under 35 U.S.C. 154(b) by 234 days.

This patent is subject to a terminal disclaimer.

(21) Appl. No.: 15/546,064

(22) PCT Filed: Jan. 26, 2016

(86) PCT No.: PCT/EP2016/051530
§ 371 (c)(1),
(2) Date: Jul. 25, 2017

(87) PCT Pub. No.: WO2016/120250
PCT Pub. Date: Aug. 4, 2016

(65) Prior Publication Data
US 2018/0009844 A1    Jan. 11, 2018

(30) Foreign Application Priority Data

Jan. 30, 2015 (EP) .................................... 15153278

(51) Int. Cl.
| | |
|---|---|
| *C07K 5/062* | (2006.01) |
| *A23L 27/00* | (2016.01) |
| *A23L 27/20* | (2016.01) |
| *A23L 23/10* | (2016.01) |
| *A23L 27/21* | (2016.01) |
| *C07H 7/02* | (2006.01) |

(52) U.S. Cl.
CPC .......... *C07K 5/06026* (2013.01); *A23L 23/10* (2016.08); *A23L 27/2052* (2016.08); *A23L 27/21* (2016.08); *A23L 27/215* (2016.08); *A23L 27/88* (2016.08); *C07H 7/02* (2013.01)

(58) Field of Classification Search
CPC ...... C07K 5/06026; C07H 15/26; C07H 7/02; A23L 23/10; A23L 23/00; A23L 27/23; A23L 27/88; A23L 27/215; A23L 27/21
See application file for complete search history.

(56) References Cited

FOREIGN PATENT DOCUMENTS

| EP | 1252825 A1 * | 10/2002 |
|---|---|---|
| EP | 2119372 | 11/2009 |

OTHER PUBLICATIONS

Lowy, P.H., Borsook, H. 1956. "Preparation of N-substituted 1-Amino-1-deoxy-D-arabino-hexuloses of Arginine, Histidine and Lysine." J. Am. Chem. Soc., vol. 78, pp. 3175-3176.*
Mossine, V.V., Mawhinney, T.P. 2007. "Nα-(1-Deoxy-D-fructos-1-yl)-L-histidine ("D-Fructose-L-histidine"): a Potent Copper Chelator from Tomato Powder." J. Agric. Food Chem., vol. 55, pp. 10373-10381.*
Ryu, K., Ide, N., Matsurra, H., Itakura, Y. 2001. "Nα-(1-Deoxy-D-fructos-1-yl)-L-Arginine, an Antioxidant Compound Identified in Aged Garlic Extract." J. Nut. vol. 131, pp. 972S-976S.*
Seifert, S.T., Krause, R., Gloe, K., Henle, T. 2004. "Metal Complexation by the Peptide-Bound Maillard Reaction Products Nε-Fructoselysine and Nε-Carboxymethyllysine." J. Agric. Food Chem. vol. 52, pp. 2347-2350.*
Sonntag et al. "Sensory-Guided Identification of N-(1-Methyl-4-oxoimidazolidin-2-ylidene)-α-amino Acids as Contributors to the Thick-Sour and Mouth-Drying Orosensation of Stewed Beef Juice" Journal of Agricultural and Food Chemistry, 2010, vol. 58, pp. 6341-6350.
Dunkel et al. "Sensory-Directed Identification of β-Alanyl Dipeptides as Contributors to the Thick-Sour and White-Meaty Orosensation Induced by Chicken Broth" Journal of Agricultural and Food Chemistry, 2009, vol. 57, pp. 9867-9877.
Ciencialova et al. "Mapping the peptide and protein immune response in the larvae of the fleshfly Sarcophaga bullata" Journal of Peptide Science, 2008, vol. 14, pp. 670-682.

* cited by examiner

*Primary Examiner* — Nikki H. Dees
(74) *Attorney, Agent, or Firm* — K&L Gates LLP

(57) ABSTRACT

The present invention relates to compounds and compositions for use in enhancing flavor and umami taste of food products. Particularly, the present invention relates to compounds of the general formula (I) and compositions comprising them.

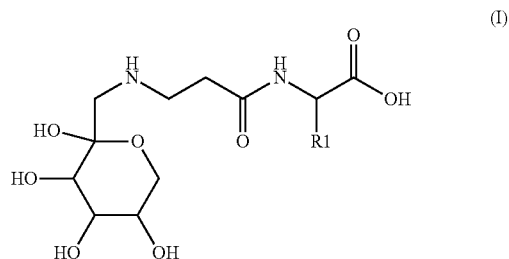

(I)

8 Claims, No Drawings

SUGAR-DIPEPTIDE CONJUGATES AS FLAVOR MOLECULES

CROSS REFERENCE TO RELATED APPLICATIONS

The present application is a National Stage of International Application No. PCT/EP2016/051530, filed on Jan. 26, 2016, which claims priority to European Patent Application No. 15153278.5, filed on Jan. 30, 2015, the entire contents of which are being incorporated herein by reference.

The present invention relates to compounds and compositions for use in enhancing flavor and umami taste of food products.

Many foods that are consumed today are rich in umami taste. Umami represents the taste of the amino acid L-glutamate and 5'-ribonucleotides such as guanosine 5'-monophosphate (GMP) and 5'-inosine monophosphate (IMP) and is sometimes also called the fifth taste. The word umami derives from the Japanese for delicious and the umami taste can be described as "savoury", "brothy" or "meaty" taste. The sensation of umami is due to the activation of taste receptor cells assembled into taste buds, distributed across different papillae of the tongue and the palate epithelium (Chandrashekar et al., 2006, Nature, 444, 288-294). Its effect is to balance taste and round out the overall flavor of a dish. Furthermore, umami enhances the palatability of a wide variety of food products. Naturally occurring glutamate can be found for example in many meat and vegetable food preparations (Ghirri et al., 2012, International Journal of Food Sciences and Nutrition, 63(7), 872-881.).

Umami or savoury, meaty taste of a food product can be further achieved and/or enhanced by adding separately monosodium glutamate (MSG) and/or the ribonucleotides GMP and IMP into those culinary recipes. Many taste enhancers comprising such MSG and/or ribonucleotides have been developed by the food industry and are available world-wide in the trade. A wide variety of ready-to-use taste enhancers are therefore available for various different culinary applications and in various different forms such as pastes, powders, liquids, compressed cubes or granules.

The addition of those culinary additives helps to provide deliciousness and enhanced taste appealing properties to food products to which they were added. Indeed, all around the world, deliciousness and appealing taste is perceived as one of the key attributes of a high quality meal. However, in many parts of the world, the addition of MSG and/or ribonucleotides has received bad press and is more and more negatively perceived by consumers. Although MSG and those ribonuleotides are naturally occurring in many food products, such as in tomatoes and meat products, and have been proven to be safe by several organizations including the World Health Organisation (WHO) and the European Food Safety Authority (EFSA), a publication in the New England Journal of Medicine (Kwok, R H M, 1968 New England Journal of Medicine, 278 (14), 796) sparked speculation among consumers about detrimental effects of MSG and ribonucleotides leading many consumers to reject products containing large amounts of such added compounds. There is therefore a strong need for industrial solutions allowing reducing the use of added MSG and ribonucleotides to food or taste enhancing products, without however compromising on umami taste and still ensuring savory superiority of such culinary products.

For example, in a recent scientific publication from A. Dunkel and T. Hofmann (Dunkel and Hofmann, 2009, J. Agric. Food Chem. 2009, 57, 9867-9877), sensory-directed fractionation of a freshly prepared double-boiled chicken soup led to the identification of β-alanylglycine as a contributor to the thick-sour and white-meaty orosensation. Quantitative analysis, followed by taste recombination and omission experiments, revealed for the first time that, when present together with L-glutamic acid and sodium and/or potassium ions, sub-threshold concentrations of this β-alanylglycine enhance the typical thick-sour orosensation and white-meaty character known for poultry meat. This is a first step in finding new compounds which are able to impart flavour richness and enhance the umami taste effect of MSG, and thereby allowing a reduced use of MSG.

SUMMARY OF THE INVENTION

The object of the present invention is to improve the state of the art and to provide an alternative or improved solution to the prior art to overcome at least some of the inconveniences described above. Particularly, the object of the present invention is to provide an alternative or improved solution for enhancing the flavour and/or umami taste of a food product.

The object of the present invention is achieved by the subject matter of the independent claims. The dependent claims further develop the idea of the present invention.

Accordingly, the present invention provides in a first aspect a compound of the general formula I,

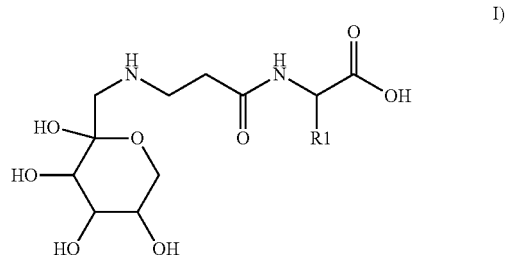

wherein R1 is a hydrogen, a $C_1$, a $C_2$, or a $C_3$ alkyl group; or a salt of said compound.

In a second aspect, the invention relates to a composition comprising said compound of the general formula I) in an amount of at least 1 mg/g, at least 1.4 mg/g, at least 1.7 mg/g, at least 2 mg/g, at least 2.5 mg/g, at least 3 mg/g, at least 3.5 mg/g, or at least 5 mg/g of the total composition.

Further aspects of the present invention relate to a use of said compound for enhancing the flavor and/or the umami taste of a food product.

Still further aspects of the present invention relate to a use of a composition comprising said compound in an amount of at least 1 mg/g, at least 1.4 mg/g, at least 1.7 mg/g, at least 2 mg/g, at least 2.5 mg/g, at least 3 mg/g, at least 3.5 mg/g, or at least 5 mg/g, for enhancing the flavor and/or the umami taste of a food product.

A still further aspect of the present invention is a method for enhancing the flavor and/or umami taste of a culinary food product, comprising the step of adding said compound or the composition comprising said compound to a food product.

The inventors surprisingly found that some sugar conjugates of β-alanyl dipeptides have a much stronger flavor enhancing effect than their corresponding aglycones. In fact, these sugar conjugates enhance umami perception and induce a thick-sour and white meaty orosensation of a culinary recipe at much lower threshold levels than their corresponding aglycones. The sugar-β-alanyl dipeptide molecules are typically generated in-situ during thermal processing of food raw materials by condensation of glucose with a β-alanyl dipeptide. The aglycones, i.e. the β-alanyl dipeptides, have been identified for example in stewed beef juice or in chicken broth and have been previously described as inducing thick-sour and mouth-drying orosensation (Sonntag et al., 2010, J. Agric. Food Chem. 58, 6341-6350; Dunkel et al., 2009, J. Agric. Food Chem., 57, 9867-9877). However, the taste enhancing threshold levels of these specific β-alanyl dipeptides are much higher than the ones of their corresponding sugar conjugates. Evidence thereof is provided in the Example section below. Therefore, the molecules described in the present invention are more potent flavor and umami taste enhancers than the known β-alanyl dipeptides. They allow further reducing the amounts and uses of MSG and/or ribonucleotides in culinary food products without compromising flavor richness and/or reducing the typical and well desired umami taste of said products. They also allow generating umami savory food concentrates which have much less or no MSG and/or ribonucleotides and still provide a strong and typical umami taste if applied to a food product. It even allows generating such umami savory food concentrates which are much stronger and more concentrated in providing an umami taste to a food product upon application.

DETAILED DESCRIPTION OF THE INVENTION

The present invention pertains to a compound of the general formula I), wherein R1 is a hydrogen, a $C_1$, a $C_2$, or a $C_3$ alkyl group; or a salt of said compound. In one embodiment, the R1 group of the compound of the present invention is a hydrogen. The chemical name of the corresponding compound is: 1-deoxy-D-fructosyl-N-β-alanyl-L-glycine.

A second aspect of the invention relates to a composition comprising said compound of the general formula I) in an amount of at least 1 mg/g, at least 1.4 mg/g, at least 1.7 mg/g, at least 2 mg/g, at least 2.5 mg/g, at least 3 mg/g, at least 3.5 mg/g, or at least 5 mg/g of the total composition.

In one embodiment, the composition of the present invention is an extract from plant and/or meat material. For example, the composition is an extract from beef meat, chicken meat, pork meat or a combination thereof.

In another embodiment, the composition of the present invention is the result of a flavor reaction. The term "flavor reaction" refers herein to a chemical reaction occurring between at least one reducing sugar and at least one amino acid or protein. Typically, this chemical reaction occurs during a heating process and is typically also referred to as Maillard reaction. In one example, the flavor reaction is a Maillard reaction.

In a preferred embodiment, the composition of the present invention is food grade. Under "food grade" the inventors mean that the composition is suitable for human consumption, for example directly, in concentrated form, and/or when used diluted in a food product.

For example, the composition of the present invention is selected from the group consisting of a culinary seasoning product, a cooking aid, a sauce or soup concentrate, a dry or wet pet-food product.

Further aspects of the present invention relate to a use of said compound for enhancing the flavor and/or the umami taste of a food product. Such a food product may be a ready-to-eat food product. It may also be a flavor concentrate used for seasoning a still further other food product. Advantageously, the compound of the present invention may be used for being added to a seasoning, a cooking aid or a food concentrate product. Thereby the strength of providing an umami taste to a still further food product is improved in such a seasoning, cooking aid or food concentrate product.

Further aspects of the present invention also relate to a use of a composition comprising said compound in an amount of at least 1 mg/g, at least 1.4 mg/g, at least 1.7 mg/g, at least 2 mg/g, at least 2.5 mg/g, at least 3 mg/g, at least 3.5 mg/g, or at least 5 mg/g of the total composition, for enhancing the flavor and/or the umami taste of a food product.

Advantageously, such a food product may be a ready-to-eat food product. The use of the present invention has the advantage that it allows to use natural extracts which for example have been enriched in said compounds for flavoring and improving the natural umami taste of those food products.

A still further aspect of the present invention is a method for enhancing the flavor and/or umami taste of a culinary food product, comprising the step of adding said compound or the composition comprising said compound to a food product. The food product can be a ready-to-eat food product or a flavor concentrate.

As an example of the present invention, the final concentration of said compound in the food product is at least 1 mg/g, at least 1.4 mg/g, at least 1.7 mg/g, at least 2 mg/g, at least 2.5 mg/g, at least 3 mg/g, at least 3.5 mg/g, or at least 5 mg/g of the composition. This advantageously, allows generating for example food seasoning products and flavor concentrate products which convey a strong umami taste to a further food product upon application.

Those skilled in the art will understand that they can freely combine all features of the present invention disclosed herein. In particular, features described for the products of the present invention may be combined with the uses and method of the present invention, and vice versa. Further, features described for different embodiments of the present invention may be combined.

Further advantages and features of the present invention are apparent from the figures and examples.

Example 1: Synthesis of 1-deoxy-D-fructosyl-N-β-alanyl-L-glycine from Glucose and β-alanyl-L-glycine Chemicals: Sodium bisulphite and glycerol were purchased from Sigma, glucose from SDfine Chemicals, β-alanylglycine from Aksci, methanol and acetic acid from Merck. All commercially available reagents were used as received, from their respective suppliers.

$^1$H NMR (360.13 MHz) and $^{13}$C NMR (90.56 MHz) spectra were recorder on a Bruker DPX-360 spectrometer equipped with a broadband multinuclear z-gradient probehead. The chemical shifts (in ppm) were expressed with respect to an internal reference (TMS or TSP). Multiplicities are reported as follows: s=singlet, d=doublet, t=triplet, q=quatruplet, m=multiplet, bs=broad singlet.

D-Glucose (23 g, 127.37 mmol, 2.8 eq) and sodium bisulfite (1.6 g, 12.389 mmol, 0.28 eq.) were suspended in methanol (38 mL) and glycerol (19 mL). After stirring for 30 min at 100° C., β-alanine-L-glycine (6.7 g, 45.48 mmol, 1.0 eq.) and acetic acid (5.1 mL) were added and the resulting mixture was heated for 3.5 hours at 100° C. Reaction mass was then cooled down and diluted with water (38 mL). The reaction mixture was purified using a column packed in Amberlite IRN-77 ion exchange resin (100 g). NH$_3$ 0-0.4% was used as gradient in water for elution. Finally, 5 g 1-deoxy-D-fructosyl-N-β-alanyl-L-glycine was obtained (23.62%).

LC-MS (ESI$^+$): m/z 309.22 (100, [M+H]$^-$); $^1$H NMR (400 MHz, 300 K, Deuterium Oxide) δ 2.80 [t, J=6.5 Hz, 2H], 3.29-3.36 [m, 2H], 3.42 [t, J=6.5 Hz, 2H], 3.72-3.77 [m, 2H], 3.78 [s, 2H], 3.89 [dd, J=3.4, 9.8 Hz, 1H], 3.99-4.05 [m, 2H]. $^{13}$C NMR (100 MHz, 300 K, Deuterium Oxide) δ 30.40, 43.18, 44.51, 53.04, 63.96, 68.85, 69.26, 69.77, 95.28, 172.13, 176.62.

Example 2: Sensory Evaluation of β-Alanyl-L-Glycine in Model Broth

The sensory tests were performed in a sensory panel room at 20-25° C. To avoid a retro-nasal aroma or taste impression, nose clips were used. The sensory panel consisted of 8 to 14 trained persons. The panel was trained to evaluate the taste of aqueous solutions (1 mL each) of the following standard taste compounds by using a triangle test: saccharose (50 mmol/L) and L-alanine (15 mmol/L), respectively, for sweet taste; lactic acid (20 mmol/L) for sour taste; NaCl (12 mmol/L) for salty taste; caffeine (1 mmol/L) and quinine hydrochloride (0.05 mmol/L), respectively, for bitter taste; sodium glutamate (8 mmol/L, pH 5.7) for umami taste; and tannin (0.05%) for astringency. The "white meaty" oral sensations was assessed in a model broth solution prepared from monosodium glutamate monohydrate (1.9 g/L), yeast extract (2.1 g/L), maltodextrin (6.375 g/L) and sodium chloride (2.9 g/L) in bottled water (pH 5.9).

The taste threshold concentration of β-alanyl-L-glycine was determined in model broth and was found to be 18,400 μmol/L (2.6 mg/g) for the thick-sour sensation and white-meaty oral impression.

Example 3: Sensory Evaluation of 1-deoxy-D-fructosyl-N-β-alanyl-L-glycine in Model Broth The taste threshold concentration of 1-deoxy-D-fructosyl-N-β-alanyl-L-glycine was determined in model broth as described in Example 2 and was found to be 4,620 μmol/L (1.4 mg/g) for the thick-sour sensation and white-meaty oral impression under the same experimental model system (see Example 2). In fact, it corresponds to a lowering of the taste threshold molar concentration by a factor of about 4.

This result means that about a 4-time smaller amount of molecules of 1-deoxy-D-fructosyl-N-β-alanyl-L-glycine is required to impart a same corresponding taste impact of flavour and umami taste enhancement in a food product than with the corresponding β-alanyl-L-glycine under the same conditions.

Example 4: Seasoning Compositions

Chicken soups were prepared by dissolving 6 g chicken base powder (detailed recipe shown in Table 1) and 1 g monosodium glutamate in 500 mL hot water. 1-Deoxy-D-fructosyl-N-β-alanyl-L-glycine was added at 2 g/L.

TABLE 1

Composition of chicken base powder

| Ingredient | Quantity (%) |
| --- | --- |
| Chicken Meat powder | 30 |
| Starch | 1.52 |
| Flavors | 2.58 |
| Celery powder | 0.50 |
| Garlic powder | 0.90 |
| Chicken fat | 8.00 |
| Maltodextrine | 56.50 |
| Total | 100 |

The sensory evaluation was carried out by 12 panelists, previously screened for their sensory abilities. The panelists were asked to taste a set of 2 chicken soups, one containing no 1-Deoxy-D-fructosyl-N-β-alanyl-L-glycine and one containing 1-Deoxy-D-fructosyl-N-β-alanyl-L-glycine at 2 g/L. If sensory differences were observed, the panelists were asked to describe them.

The sensory panel concluded that chicken soups with and without the 1-Deoxy-D-fructosyl-N-β-alanyl-L-glycine were perceived as significantly different and the addition of 1-Deoxy-D-fructosyl-N-β-alanyl-L-glycine increased the spicy, savory and meaty flavours.

Example 5: Seasoning Compositions

Tomato soups were prepared by dissolving in 6 g tomato base powder (detailed recipe shown in the Table 2) in 500 mL hot water. 1-Deoxy-D-fructosyl-N-β-alanyl-L-glycine was added at 2 g/L.

TABLE 2

Composition of tomato soup powder

| Ingredient | Quantity (g) |
| --- | --- |
| Yeast extract | 0.036 |
| White Sugar | 0.348 |
| Flavors | 0.629 |
| Tomato powder | 0.03 |
| Wheat flour | 0.562 |
| Corn starch | 0.247 |
| Guar gum | 0.012 |
| Spices powder | 0.071 |
| Maltodextrine | 0.038 |
| Sunflower oil | 0.022 |
| Total | 2 |

The sensory panel concluded that tomato soups with and without the 1-Deoxy-D-fructosyl-N-β-alanyl-L-glycine were perceived as significantly different and the addition of 1-deoxy-D-fructosyl-N-β-alanine increased the savory, fatty and spicy notes.

The invention claimed is:

1. A composition comprising a compound of the general formula I,

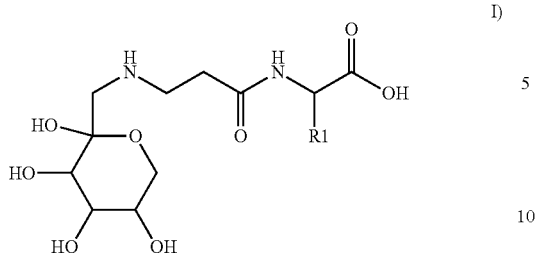

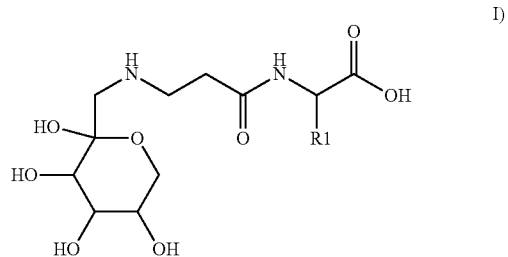

wherein R1 is selected from the group consisting of a hydrogen, a $C_1$, a $C_2$, a $C_3$, and a $C_4$ alkyl group, or a salt of the compound, the composition is selected from the group consisting of a culinary seasoning, a sauce or soup concentrate, and a dry or wet pet-food product, and a final concentration of the compound in the composition is 1 mg/g to 3 mg/g.

2. The composition according to claim 1, wherein the composition is an extract from a plant and/or meat material.

3. The composition according to claim 1, wherein the composition is resultant from a flavor reaction.

4. A method for enhancing a flavor and/or umami taste of a culinary food product, the method comprising adding a compound of the general formula I, wherein R1 is selected from the group consisting of a hydrogen, a $C_1$, a $C_2$, a $C_3$, and a $C_4$ alkyl group, or a salt of the compound to the culinary food product, and a final concentration of the compound in the culinary food product is 1 mg/g to 3 mg/g.

5. The composition of claim 1, wherein the final concentration of the compound in the composition is 1 mg/g to 2.5 mg/g.

6. The composition of claim 1, wherein the final concentration of the compound in the composition is 1 mg/g to 2.0 mg/g.

7. The method of claim 4, wherein the final concentration of the compound in the culinary food product is 1 mg/g to 2.5 mg/g.

8. The method of claim 4, wherein the final concentration of the compound in the culinary food product is 1 mg/g to 2.0 mg/g.

\* \* \* \* \*